(12) United States Patent
Healy et al.

(10) Patent No.: US 7,718,689 B2
(45) Date of Patent: *May 18, 2010

(54) BENZOISOINDOLE DERIVATIVES AND THEIR USE AS EP4 RECEPTOR LIGANDS

(75) Inventors: Mark Patrick Healy, Harlow (GB); Gerard Martin Paul Giblin, Harlow (GB); Neil Derek Miller, Singapore (SG)

(73) Assignee: Glaxo Group Limited, Greenford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/278,979

(22) PCT Filed: Feb. 12, 2007

(86) PCT No.: PCT/EP2007/051348

§ 371 (c)(1),
(2), (4) Date: Aug. 11, 2008

(87) PCT Pub. No.: WO2007/093578

PCT Pub. Date: Aug. 23, 2007

(65) Prior Publication Data
US 2009/0030061 A1  Jan. 29, 2009

(30) Foreign Application Priority Data
Feb. 13, 2006 (GB) ................... 0602900.3

(51) Int. Cl.
*A61K 31/4035* (2006.01)
*C07D 209/60* (2006.01)

(52) U.S. Cl. ..................... 514/411; 548/427

(58) Field of Classification Search ............. 514/411; 548/427
See application file for complete search history.

(56) References Cited

U.S. PATENT DOCUMENTS
2008/0234358 A1 *  9/2008  Congreve

FOREIGN PATENT DOCUMENTS
| WO | 0250033 A | 6/2002 |
| WO | WO 0250033 | * 6/2002 |
| WO | 02064564 A | 8/2002 |

* cited by examiner

Primary Examiner—Kamal A Saeed
Assistant Examiner—Janet L Coppins
(74) Attorney, Agent, or Firm—Bonnie L. Deppenbrock

(57) ABSTRACT

A compound of formula (I) or a pharmaceutically acceptable derivative thereof,

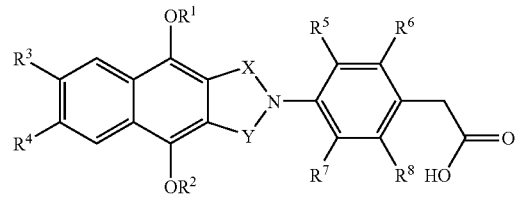

(I)

wherein $R^1$ to $R^8$, X, and Y are as defined in the specification; a process for preparing such compounds; a pharmaceutical composition comprising such compounds; and the use of such compounds in medicine.

16 Claims, No Drawings

BENZOISOINDOLE DERIVATIVES AND THEIR USE AS EP4 RECEPTOR LIGANDS

CROSS-REFERENCE TO RELATED APPLICATIONS

This application is filed pursuant to 35 USC 371 as a United States National Phase Application of International Patent Application Serial No. PCT1EP20071051348 filed on Feb. 12, 2007, which claims priority from 0602900.3 filed on Feb. 13, 2006 in the United Kingdom.

FIELD OF THE INVENTION

This invention relates to naphthalene derivatives, to processes for their preparation, to pharmaceutical compositions containing them and to their use in medicine.

The compounds of the present invention are $EP_4$ receptor agonists.

BACKGROUND OF THE INVENTION

A number of review articles describe the characterization and therapeutic relevance of the prostanoid receptors as well as the most commonly used selective agonists and antagonists: *Eicosanoids; From Biotechnology to Therapeutic Applications*, Folco, Samuelsson, Maclouf, and Velo eds, Plenum Press, New York, 1996, chap. 14, 137-154 and Journal of Lipid Mediators and Cell Signalling, 1996, 14, 83-87 and *Prostanoid Receptors, Structure, Properties and Function*, S Narumiya et al, Physiological Reviews 1999, 79(4), 1193-126.

The $EP_4$ receptor is a 7-transmembrane receptor and its natural ligand is the prostaglandin $PGE_2$. $PGE_2$ also has affinity for the other EP receptors (types $EP_1$, $EP_2$ and $EP_3$). The prostanoid $EP_4$ receptor falls into a group of receptors normally associated with elevation of intracellular cyclic adenosine monophosphate (cAMP) levels. The $EP_4$ receptor is associated with smooth muscle relaxation, intraocular pressure, pain (in particular inflammatory, neuropathic and visceral pain), inflammation, neuroprotection, lymphocyte differentiation, bone metabolic processes, allergic activities, promotion of sleep, renal regulation, gastric or enteric mucus secretion and duodenal bicarbonate secretion. The $EP_4$ receptor plays an important role in closure of the ductus arteriosus, vasodepression, inflammation and bone remodeling as reviewed by Narumiya in *Prostaglandins & Other Lipid Mediators* 2002, 68-69 557-73.

A number of publications have demonstrated that $PGE_2$ acting through the $EP_4$ receptor subtype, and $EP_4$ agonists alone, can regulate inflammatory cytokines after an inflammatory stimulus. Takayama et al in the *Journal of Biological Chemistry* 2002, 277(46), 44147-54 showed $PGE_2$ modulates inflammation during inflammatory diseases by suppressing macrophage derived chemokine production via the $EP_4$ receptor. In *Bioorganic & Medicinal Chemistry* 2002, 10(7), 2103-2110, Maruyama et al demonstrate the selective $EP_4$ receptor agonist (ONO-AE1-437) suppresses LPS induced TNF-α in human whole blood whilst increasing the levels of IL-10. An article from *Anesthesiology*, 2002, 97, 170-176 suggests that a selective $EP_4$ receptor agonist (ONO-AE1-329) effectively inhibited mechanical and thermal hyperalgesia and inflammatory reactions in acute and chronic monoarthritis.

Two independent articles from Sakuma et al in *Journal of Bone and Mineral Research* 2000, 15(2), 218-227 and Miyaura et al in *Journal of Biological Chemistry* 2000, 275 (26), 19819-23, report impaired osteoclast formation in cells cultured from $EP_4$ receptor knock-out mice. Yoshida et at in *Proceedings of the National Academy of Sciences of the United States of America* 2002, 99(7), 4580-4585, by use of mice lacking each of the $PGE_2$ receptor EP subtypes, identified $EP_4$ as the receptor that mediates bone formation in response to $PGE_2$ administration. They also demonstrated a selective $EP_4$ receptor agonist (ONO-4819) consistently induces bone formation in wild type mice. Additionally, Terai et al in *Bone* 2005, 37(4), 555-562 have shown the presence of a selective $EP_4$ receptor agonist (ONO-4819) enhanced the bone-inducing capacity of rhBMP-2, a therapeutic cytokine that can induce bone formation.

Further research by Larsen et al shows the effects of $PGE_2$ on secretion in the second part of the human duodenum is mediated through the $EP_4$ receptor (*Acta. Physiol. Scand.* 2005, 185, 133-140). Also, it has been shown a selective $EP_4$ receptor agonist (ONO-AE1-329) can protect against colitis in rats (Nitta et al. in *Scandinavian Journal of Immunology* 2002, 56(1), 66-75).

Doré et al in *The European Journal of Neuroscience* 2005, 22(9), 2199-206 have shown that $PGE_2$ can protect neurons against amyloid beta peptide toxicity by acting on $EP_2$ and $EP_4$ receptors. Furthermore Doré has demonstrated in *Brain Research* 2005, 1066(1-2), 71-77 that an $EP_4$ receptor agonist (ONO-AE1-329) protects against neurotoxicity in an acute model of excitotoxicity in the brain.

Woodward et al in Journal of Lipid Mediators 1993, 6(1-3), 545-53 found intraocular pressure could be lowered using selective prostanoid agonists. Two papers in Investigative Opthalmology & Visual Science have shown the prostanoid $EP_4$ receptor is expressed in human lens epithelial cells (Mukhopadhyay et al 1999, 40(1), 105-12), and suggest a physiological role for the prostanoid $EP_4$ receptor in modulation of flow in the trabecular framework of the eye (Hoyng et a/1999, 40(11), 2622-6).

Compounds exhibiting $EP_4$ receptor binding activity and their uses have been described in, for example, WO98/55468, WO00/18744, WO00/03980, WO00/15608, WO00/16760, WO00/21532, WO01010426, EP0855389, EP0985663, WO02/047669, WO02/50031, WO02/50032, WO02/50033, WO02/064564, WO03/103604, WO03/077910, WO03/086371, WO04/037813, WO04/067524, WO04/085430, US04/142969, WO05/021508, WO05/105733, WO05/105732, WO05/080367, WO05/037812, WO05/116010 and WO06/122403.

Derivatives of indoprofen such as [4-(1-oxo-1,3-dihydro-2H-benzo[f]isoindol-2-yl)phenyl]-2-propionic acid, sodium salt have been described by Rufer et. al. in *Eur. J. Med. Chem.—Chimica Therapeutica*, 1978, 13, 193.

DESCRIPTION OF THE INVENTION

The present invention provides compounds of formula (I) and/or pharmaceutically acceptable derivatives thereof,

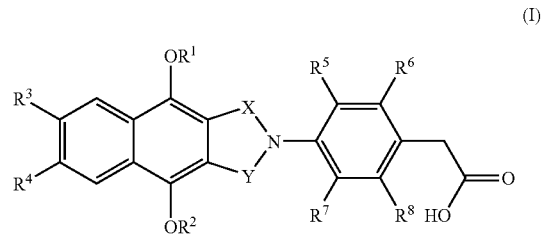

(I)

wherein, $R^1$ and $R^2$ independently represent $C_{1-4}$ alkyl or $C_{1-4}$ haloalkyl;

$R^3$ and $R^4$ independently represent H or F, provided that at least one of $R^3$ and $R^4$ represents F;

$R^5$ and $R^7$ independently represent H, methyl, methoxy, F, Cl or Br;

$R^6$ and $R^8$ independently represent H or F, provided that when one of $R^6$ or $R^8$ represents F then the adjacent atom $R^5$ or $R^7$ represents H; and X and Y independently represent C=O or $CH_2$, provided that at least one of X and Y represents C=O.

In one embodiment of the invention $R^1$ and $R^2$ independently represent $C_{1-4}$ alkyl or $C_{1-4}$ fluoroalkyl. In one embodiment of the invention $R^1$ and $R^2$ are the same and represent $C_{1-4}$ alkyl. In another embodiment of the invention $R^1$ and $R^2$ represent ethyl.

In one embodiment of the invention $R^3$ represents H and $R^4$ represents F. In another embodiment of the invention $R^3$ represents F and $R^4$ represents H. In another embodiment of the invention both $R^3$ and $R^4$ represent F.

In one embodiment of the invention $R^5$ and $R^7$ represent H. In another embodiment of the invention one of $R^5$ or $R^7$ represents H and the other represents methyl, methoxy, F, Cl or Br. In one embodiment of the invention both $R^5$ and $R^7$ independently represent methyl, methoxy, F, Cl or Br.

In one embodiment of the invention $R^6$ and $R^8$ represent H. In another embodiment of the invention one of $R^6$ or $R^8$ represents H and the other represents F.

In one embodiment of the invention $R^5$, $R^6$, $R^7$ and $R^8$ represent H.

In one embodiment of the invention X represents C=O and Y represents $CH_2$. In another embodiment X represents $CH_2$ and Y represents C=O. In another embodiment of the invention both X and Y represent C=O.

In another embodiment of the invention there is provided a subset of compounds of formula (I), of formula (IA) and/or pharmaceutically acceptable derivatives thereof, (IA)

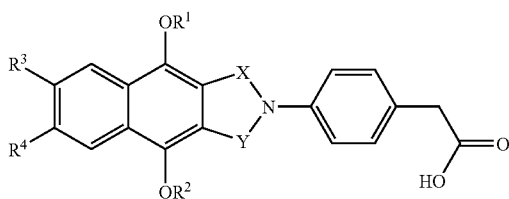

wherein, $R^1$ and $R^2$ independently represent $C_{1-4}$ alkyl;

$R^3$ and $R^4$ independently represent H or F, provided that they are not the same and that at least one of $R^3$ and $R^4$ represents F; and X and Y independently represent C=O or $CH_2$, provided that at least one of X and Y represents C=O.

In another embodiment of the invention there is provided a compound of formula (I) selected from the group consisting of:

{4-[4,9-bis(ethyloxy)-6-fluoro-1-oxo-1,3-dihydro-2H-benzo[f]isoindol-2-yl]phenyl}acetic acid;

{4-[4,9-bis(ethyloxy)-6-fluoro-1,3-dioxo-1,3-dihydro-2H-benzo[f]isoindol-2-yl]phenyl}acetic acid; and {4-[4,9-bis(ethyloxy)-7-fluoro-1-oxo-1,3-dihydro-2H-benzo[f]isoindol-2-yl]phenyl}acetic acid; or a pharmaceutically acceptable derivative thereof.

The present invention covers all combinations of the embodiments as described herein.

As used herein, the term '$C_{1-4}$ alkyl' includes straight chain and branched chain alkyl groups containing 1 to 4 carbon atoms, such as methyl, ethyl, n-propyl, iso-propyl, n-butyl, iso-butyl and tert-butyl.

As used herein, F means fluoro, Cl means chloro and Br means bromo.

By pharmaceutically acceptable derivative is meant any pharmaceutically acceptable salt, solvate or ester, or salt or solvate of such ester of the compounds of formula (I), or any other compound which upon administration to the recipient is capable of providing (directly or indirectly) a compound of formula (I) or an active metabolite or residue thereof. In one embodiment of the invention pharmaceutically acceptable derivative means salt or solvate. In one embodiment of the invention pharmaceutically acceptable derivative means salt. In one embodiment of the invention pharmaceutically acceptable derivative means solvate.

It will be appreciated that, for pharmaceutical use, the salts referred to above will be the pharmaceutically acceptable salts, but other salts may find use, for example in the preparation of compounds of formula (I) and the pharmaceutically acceptable salts thereof.

Pharmaceutically acceptable salts include those described by Berge, Bighley and Monkhouse, *J. Pharm. Sci.*, 1977, 66, 1-19. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, Nethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropyl amine, tris(hydroxymethyl)aminomethane, and the like. Salts may also be formed from basic ion exchange resins, for example polyamine resins.

It will be appreciated that the compound of formula (I) may be produced in vivo by metabolism of a suitable prodrug. Such prodrugs may be for example physiologically acceptable metabolically labile esters of compounds of the general formula (I). These may be formed by esterification of the carboxylic acid group in the parent compound of general formula (I) with, where appropriate, prior protection of any other reactive groups present in the molecule followed by deprotection if required. Examples of such metabolically labile esters include $C_{1-4}$alkyl esters e.g. methyl ethyl or t-butyl esters esters, C alkenyl esters e.g. allyl substituted or unsubstituted aminoalkyl esters (e.g. aminoethyl, 2-(N,N-diethylamino) ethyl, or 2-(4-morpholino)ethyl esters or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-(1-methoxy-1-methyl)ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl.

It is to be understood that the present invention encompasses all isomers of the compounds of formula (I) and their pharmaceutically acceptable derivatives, including all geometric, tautomeric and optical forms, and mixtures thereof (e.g. racemic mixtures).

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

The present invention also includes within its scope all isotopically-labelled compounds of formula (I). Such compounds are identical to those recited in formula (I) except that one or more atoms therein are replaced by an atom having an atomic mass or mass number different from the atomic mass or mass number usually found in nature. Examples of isotopes that can be incorporated into compounds of formula (I) and pharmaceutically acceptable derivatives thereof include isotopes of hydrogen, carbon, nitrogen, oxygen, fluorine, chlorine and bromine, such as 2H, 3H, 11C, 13C, 14C, 15N, 17O, 18O, 18F, 36Cl and 82Br.

Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography) and are useful in brain imaging. Further substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula (I) may be prepared by carrying out the synthetic procedures disclosed in the Schemes and/or in the Examples below, by substituting a readily available isotopically labelled reagent for a non-isotopically labelled reagent.

The compounds of the invention are $EP_4$ receptor agonists and may therefore be useful in treating $EP_4$ receptor mediated diseases.

In particular the compounds of formula (I) may be useful in the treatment of pain, for example, chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of formula (I) may be particularly useful in the treatment of neuropathic pain and symptoms associated therewith. Neuropathic pain syndromes include: diabetic neuropathy; sciatica; non-specific lower back pain; multiple sclerosis pain; fibromyalgia; HIV-related neuropathy; postherpetic neuralgia; trigeminal neuralgia; and pain resulting from physical trauma, amputation, cancer, toxins or chronic inflammatory conditions. Symptoms of neuropathic pain include spontaneous shooting and lancinating pain, or ongoing, burning pain. In addition, there is included pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD; gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease, diarrhoea, constipation); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of formula (I) may also be useful in the treatment of immunological diseases such as autoimmune diseases, immunological deficiency diseases or organ transplantation. The compounds of formula (I) may also be effective in increasing the latency of HIV infection.

The compounds of formula (I) may also be useful in the treatment of diseases of excessive or unwanted platelet activation such as intermittent claudication, unstable angina, stroke, and acute coronary syndrome (e.g. occlusive vascular diseases).

The compounds of formula (I) may also be useful as a drug with diuretic action, or may be useful to treat overactive bladder syndrome.

The compounds of formula (I) may also be useful in the treatment of impotence or erectile dysfunction.

The compounds of formula (I) may also be useful in the treatment of bone disease characterised by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, calculosis, lithiasis (especially urolithiasis), gout and ankylosing spondylitis, tendinitis and bursitis.

The compounds of formula (I) may also be useful in bone remodelling and/or promoting bone generation and/or promoting fracture healing.

The compounds of formula (I) may also be useful for attenuating the hemodynamic side effects of NSAIDs and COX-2 inhibitors.

The compounds of formula (I) may also be useful in the treatment of cardiovascular diseases such as hypertension or myocardial ischemia; functional or organic venous insufficiency; varicose therapy; haemorrhoids; and shock states associated with a marked drop in arterial pressure (e.g. septic shock).

The compounds of formula (I) may also be useful in the treatment of neurodegenerative diseases such as dementia, particularly degenerative dementia (including senile dementia, Alzheimer's disease, Pick's disease, Huntingdon's chorea, Parkinson's disease and Creutzfeldt-Jakob disease, Amyotrophic lateral sclerosis (ALS), motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) may also be useful in the treatment of neurological disorders and may be useful as neuroprotecting agents. The compounds of the invention may also be useful in the treatment of neurodegeneration following stroke, cardiac arrest, pulmonary bypass, traumatic brain injury, spinal cord injury or the like.

The compounds of formula (I) may also be useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of formula (I) may also be useful in the treatment of a kidney dysfunction (nephritis, particularly mesangial proliferative glomerulonephritis, nephritic syndrome), a liver dysfunction (hepatitis, cirrhosis) and gastrointestinal dysfunction (diarrhoea).

It is to be understood that reference to treatment includes both treatment of established symptoms and prophylactic treatment.

According to a further embodiment of the invention, there is provided a compound of formula (I) or a pharmaceutically acceptable derivative thereof for use in human or veterinary medicine.

According to another embodiment of the invention, there is provided a compound of formula (I) or a pharmaceutically acceptable derivative thereof for use in the treatment of a condition which is mediated by the action, or loss of action, of $PGE_2$ at $EP_4$ receptors.

According to a further embodiment of the invention, there is provided a method of treating a human or animal subject suffering from a condition which is mediated by the action, or by loss of action, of $PGE_2$ at $EP_4$ receptors which comprises administering to said subject an effective amount of a compound of formula (I) or a pharmaceutically acceptable derivative thereof.

According to a further embodiment of the invention there is provided a method of treating a human or animal subject suffering from a pain, or an inflammatory, immunological or bone disease, a neurodegenerative disease or a kidney dysfunction, which method comprises administering to said subject an effective amount of a compound of formula (I) or a pharmaceutically acceptable derivative thereof.

According to another embodiment of the invention, there is provided the use of a compound of formula (I) or a pharmaceutically acceptable derivative thereof for the manufacture of a medicament for the treatment of a condition which is mediated by the action of $PGE_2$ at $EP_4$ receptors.

According to another embodiment of the invention there is provided the use of a compound of formula (I) or a pharmaceutically acceptable derivative thereof for the manufacture of a medicament for the treatment or prevention of a condition such as a pain, or an inflammatory, immunological, bone, neurodegenerative or kidney disorder.

The compounds of formula (I) and their pharmaceutically acceptable derivatives are conveniently administered in the form of pharmaceutical compositions. Such compositions may conveniently be presented for use in conventional manner in admixture with one or more physiologically acceptable carriers or excipients.

Thus, in another aspect of the invention, there is provided a pharmaceutical composition comprising a compound of formula (I) or a pharmaceutically acceptable derivative thereof adapted for use in human or veterinary medicine.

While it is possible for the compounds of formula (I) or a pharmaceutically acceptable derivative thereof to be administered as the raw chemical, it is preferable to present it as a pharmaceutical formulation. The formulations of the present invention comprise the compounds of formula (I) or a pharmaceutically acceptable derivative thereof together with one or more acceptable carriers or diluents therefor and optionally other therapeutic ingredients. The carrier(s) must be "acceptable" in the sense of being compatible with the other ingredients of the formulation and not deleterious to the recipient thereof.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy (see for example methods disclosed in 'Remington—The Science and Practice of Pharmacy', 21$^{st}$ Edition, Lippincott, Williams & Wilkins, USA, 2005 and references therein). All methods include the step of bringing into association the compound of formula (I) or a pharmaceutically acceptable derivative thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

The $EP_4$ receptor compounds for use in the present invention may be used in combination with other therapeutic agents, for example COX-2 inhibitors, such as celecoxib, rofecoxib, valdecoxib or parecoxib; 5-lipoxygenase inhibitors; analgesics such as paracetamol; NSAID's, such as diclofenac, indomethacin, nabumetone, naproxen or ibuprofen; leukotriene receptor antagonists; DMARD's such as methotrexate; sodium channel blockers, such as lamotrigine; N-type calcium channel antagonists; NMDA receptor modulators, such as glycine receptor antagonists; gabapentin, pregabalin and related compounds; tricyclic antidepressants such as amitriptyline; neurone stabilising antiepileptic drugs; mono-aminergic uptake inhibitors such as venlafaxine; opioid analgesics; local anaesthetics; 5HT1 agonists, such as triptans, for example sumatriptan, naratriptan, zolmitriptan, eletriptan, frovatriptan, almotriptan or rizatriptan; $EP_1$ receptor ligands; $EP_2$ receptor ligands; $EP_3$ receptor ligands; $EP_1$ antagonists; $EP_2$ antagonists and $EP_3$ antagonists; cannabanoid receptor agonists; VR1 antagonists. When the compounds are used in combination with other therapeutic agents, the compounds may be administered either sequentially or simultaneously by any convenient route.

The invention thus provides, in a further embodiment, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease, the dose of each compound may differ from that when the compound is used alone. Appropriate doses will be readily appreciated by those skilled in the art.

A proposed daily dosage of compounds of formula (I) or their pharmaceutically acceptable salts for the treatment of man is from 0.001 to 30 mg/kg body weight per day and more particularly 0.1 to 3 mg/kg body weight per day, calculated as the free acid, which may be administered as a single or divided dose, for example one to four times per day. The dose range for adult human beings is generally from 0.1 to 1000 mg/day, such as from 10 to 800 mg/day, preferably 10 to 200 mg/day, calculated as the free acid.

The precise amount of the compounds of formula (I) administered to a host, particularly a human patient, will be the responsibility of the attendant physician. However, the dose employed will depend on a number of factors including the age and sex of the patient, the precise condition being treated and its severity, the route of administration, and any possible combination therapy that may be being undertaken.

The present invention also provides processes for preparing compounds of formula (I) and pharmaceutically acceptable derivatives thereof.

Thus, in one embodiment of the present invention there is provided a process for preparing a compound of formula (I), wherein X and Y represent C=O and $R^1$ to $R^8$ are as hereinbefore defined in relation to formula (I), which process comprises reacting a compound of formula (II),

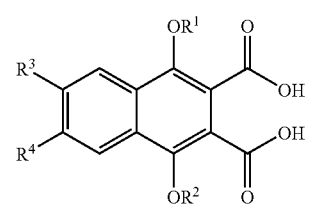

(II)

wherein, $R^1$, $R^2$, $R^3$ and $R^4$ are as hereinbefore defined in relation to formula (I), with 4-aminophenylacetic acid or a derivative thereof, and optionally thereafter forming a pharmaceutically acceptable derivative of the compound so formed and/or converting one compound of formula (I) to another.

In one embodiment the above-mentioned reaction comprising a compound of formula (II) is performed in a suitable solvent such as N-methylpyrrolidinone. In another embodiment the reaction is performed in a suitable solvent, such as N-methylpyrrolidinone, and is heated to a temperature in the range from about 150 to 200° C., such as about 180° C.

4-Aminophenylacetic acid and derivatives thereof are commercially available (e.g. Sigma-Aldrich Co. Ltd) and/or may be prepared by methods known in the art.

In another embodiment of the invention there is provided a process for preparing a compound of formula (I) wherein one of X and Y represents C=O and the other represents $CH_2$, and $R^1$ to $R^8$ are as hereinbefore defined in relation to formula (I), which process comprises reacting a compound of formula (III),

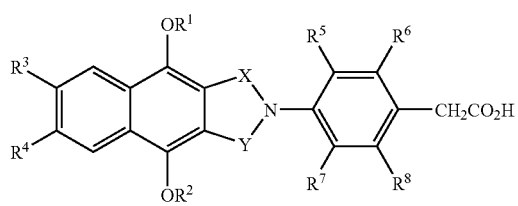

wherein, one of X and Y represents C=O and the other represents CH—OH and $R^1$ to $R^8$ are as hereinbefore defined in relation to formula (I); with a suitable acid, followed by a suitable reducing agent, and optionally thereafter forming a pharmaceutically acceptable derivative of the compound so formed and/or converting one compound of formula (I) to another.

A suitable acid is trifluoroacetic acid.

A suitable reducing agent is a trialkylsilane, such as triethylsilane.

In one embodiment the above-mentioned reaction comprising a compound of formula (III) is performed in a suitable solvent, such as dichloromethane. In another embodiment the reaction is performed in a suitable solvent, such as dichloromethane, at ambient temperature.

It will be appreciated that compounds of formula (I) may also be prepared from ester derivatives of the compounds of formula (I) by performing an additional 'deprotection' step to the reaction outlined above, using conventional acidic or basic conditions. Suitable acidic conditions include treatment with hydrochloride acid and acetic acid. Suitable basic conditions include treatment with sodium hydroxide.

Compounds of formula (II) may be prepared in accordance with Scheme 1 below:

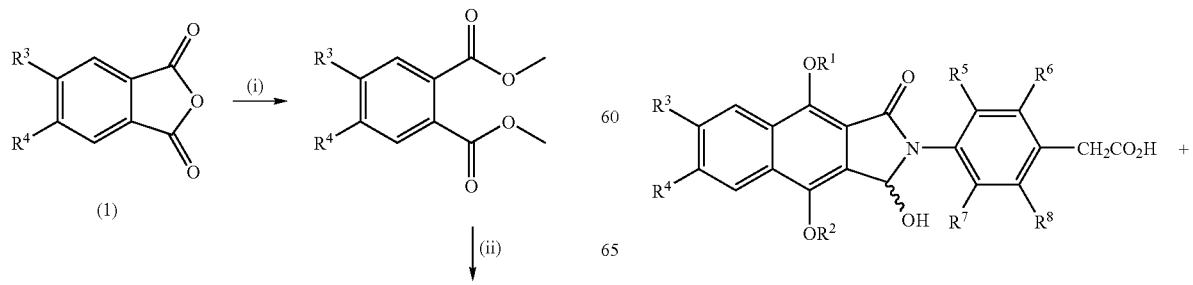

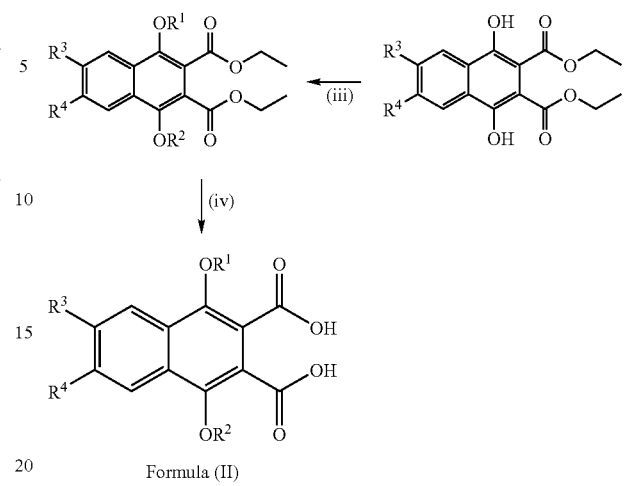

where: (i) MeOH, conc. $H_2SO_4$, reflux 48 h; (ii) Diethyl succinate, LHMDS, THF; (iii) $K_2CO_3$, $CH_3CH_2I$, $(CH_3)_2CO$; (iv) EtOH, NaOH, reflux 1 h. $R^1$, $R^2$, $R^3$ and $R^4$ are as defined in relation to Formula (II).

Compounds of formula (I) are commercially available. For example, 4-Fluorophthalic anhydride was purchased from Fluorochem UK.

Compounds of formula (III) may be prepared by reacting the corresponding 1,3-dioxo compounds of formula (I), with a suitable reducing agent such as sodium borohydride in the presence of a suitable solvent such as methanol and/or ethanol; for example as shown in Scheme 2 below:

Scheme 2

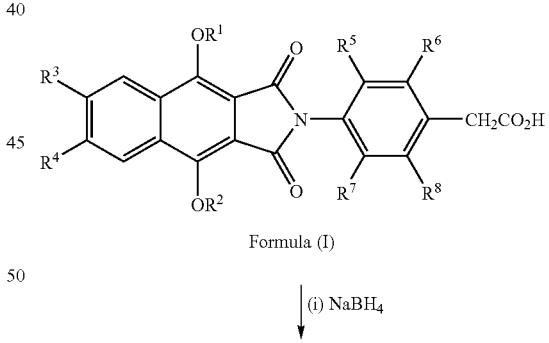

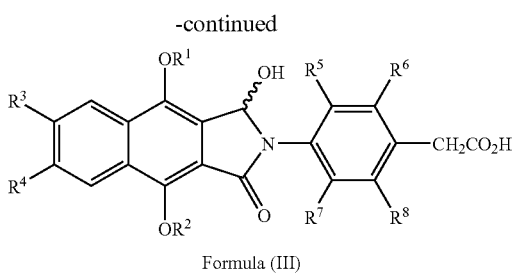

Formula (III)

It will be appreciated that when the above-mentioned reduction is performed in a solvent such as methanol and/or ethanol, methoxy and ethoxy animals of the compounds of Formula (III) are also formed. Such animals may be readily converted to compounds of formula (I) in situ by reaction with a suitable acid (such as trifluoroacetic acid) followed by a suitable reducing agent (such as triethylsilane) as described herein.

In a further embodiment of the invention there is provided a process for preparing a compound of formula (I), wherein X and Y represent C=O and $R^1$ to $R^8$ are as hereinbefore defined in relation to formula (I), which process comprises reacting a compound of formula (IV),

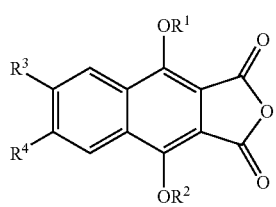

(IV)

wherein, $R^1$ to $R^4$ are as hereinbefore defined in relation to formula (I), with 4-aminophenylacetic acid or a derivative thereof, and optionally thereafter forming a pharmaceutically acceptable derivative of the compound so formed and/or converting one compound of formula (I) to another.

Compounds of formula (IV) may be prepared from compounds of formula (II) using conventional methods, for example, by treatment with $SOCl_2$ in the presence of a suitable solvent such as $CHCl_3$ or EtOH.

The following Descriptions and Examples illustrate the preparation of the compounds of the invention. Descriptions refer to intermediate compounds.

| Abbreviations | |
|---|---|
| EtOAc | Ethyl acetate |
| Et$_2$O | Diethyl ether |
| EtOH | Ethanol |
| HCl | Hydrochloric acid |
| LHMDS | Lithium hexamethyldisylazide |
| NMP | N-Methylpyrrolidinone |
| TFA | Trifluoroacetic acid |
| THF | Tetrahydrofuran |

Analytical Procedures

LC/MS

Column

Waters Atlantis (4.6 mm×50 mm). Stationary phase particle size, 3 μm.

Solvents

A: Aqueous solvent=Water+0.05% Formic Acid

B: Organic solvent=Acetonitrile+0.05% Formic Acid

Method

| Time/min | % B |
|---|---|
| 0 | 3 |
| 0.1 | 3 |
| 4 | 97 |
| 4.8 | 97 |
| 4.9 | 3 |
| 5.0 | 3 |

Flow rate, 3 ml/mins.

Injection volume, 5 μl.

Column temperature, 30° C.

UV detection range, 220 to 330 nm.

All retention times are measured in minutes.

Description 1

Dimethyl 4-fluoro-1,2-benzenedicarboxylate

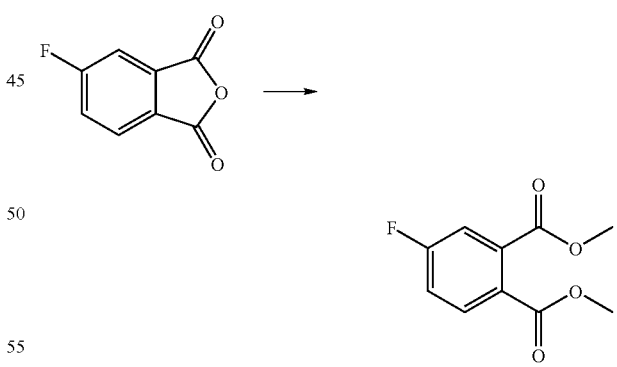

4-Fluorophthalic anhydride (7.79 g, 46.9 mmol) [Fluorochem] in methanol (80 ml) and conc. $H_2SO_4$ (1 ml) were heated at reflux for 48 hours. Cooled, basified with 880 ammonia solution (~1 ml) and concentrated in vacuo. The oil was partitioned between water and EtOAc. The organics were washed with brine, dried over magnesium sulphate and concentrated in vacuo to yield the title compound as a colourless oil (9.4 g, 44.3 mmol).

LC/MS: Rt=2.50.

Description 2

Diethyl 6-fluoro-1,4-dihydroxy-2,3-naphthalenedicarboxylate

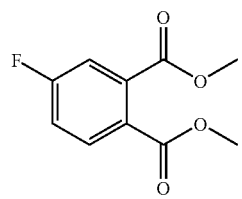
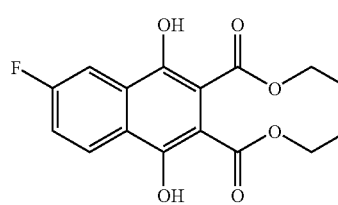

Diethyl succinate (16.26 ml, 98.1 mmol) was added to dimethyl 4-fluoro-1,2-benzenedicarboxylate (10.4 g, 49.1 mmol) and LHMDS (1M in THF, 196 ml, 196 mmol) in THF (150 ml) at 10° C. (internal) over 30 minutes. Allowed to warm to room temperature slowly. After 20 hours, 2M HCl (~500 ml) was added to acidify to pH 5. The mixture was extracted with EtOAc, then the organics washed with water, brine, dried over magnesium sulphate and concentrated in vacuo to give a brown oil. This was purified by chromatography on silica gel eluting with EtOAc/hexane (2:98) to yield the title compound as a yellow solid (4.58 g, 14.2 mmol).

LC/MS: Rt=3.50.

Description 3

Diethyl 1,4-bis(ethyloxy)-6-fluoro-Z 3-naphthalenedicarboxylate

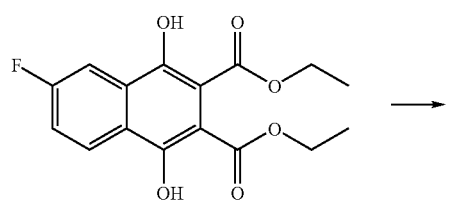
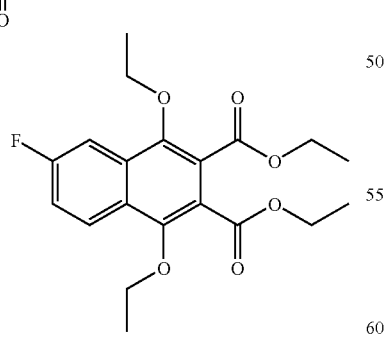

Potassium carbonate (3.85 g, 27.9 mmol) and ethyl iodide (2.24 ml, 28 mmol) were added to diethyl 6-fluoro-1,4-dihydroxy-2,3-naphthalenedicarboxylate (3 g, 9.3 mmol) in acetone (75 ml) and heated under reflux. After 20 hours the resulting mixture was cooled, volatiles removed in vacuo, diluted with water (150 ml), extracted with EtOAc (×3), the organics were washed with brine, dried over magnesium sulphate and concentrated to give a brown oil. Purified by chromatography on silica gel eluting with EtOAc/hexane (1:49-1:4) to give the title compound as yellow oil (2.77 g, 7.3 mmol).

LC/MS: Rt=3.71, [MNH$_4$]$^+$396.

Description 4

1,4-Bis(ethyloxy)-6-fluoro-2,3-naphthalenedicarboxylic acid

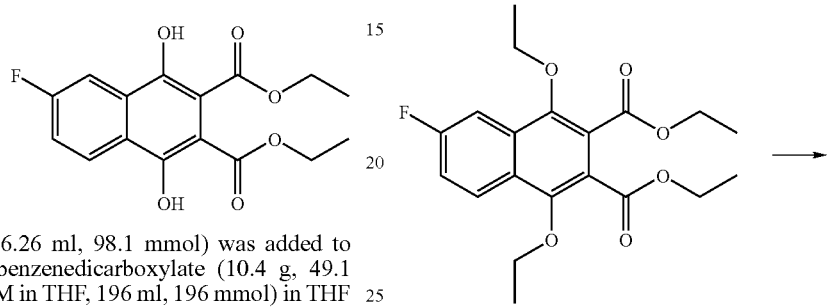
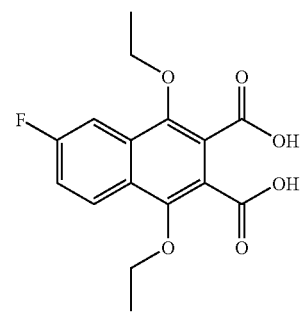

A mixture of diethyl 1,4-bis(ethyloxy)-6-fluoro-2,3-naphthalenedicarboxylate (2.5 g, 6.6 mmol), ethanol (50 ml) and sodium hydroxide (50 ml) was heated under reflux for 1 hour. The reaction mixture was cooled and concentrated in vacuo. This was acidified with 2N HCl (~50 ml) and extracted with EtOAc (×2). Combined organics were washed with brine, dried over magnesium sulphate and concentrated in vacuo to give the title compound as a yellow solid (2.24 g).

LC/MS: Rt=2.56, [MH]$^+$ 323.

Example 1

{4-[4,9-Bis(ethyloxy)-6-fluoro-1,3-dioxo-1,3-dihydro-2H-benzo[f]isoindol-2-yl]phenyl}acetic acid

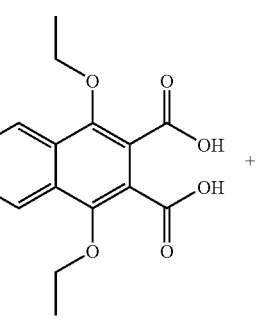

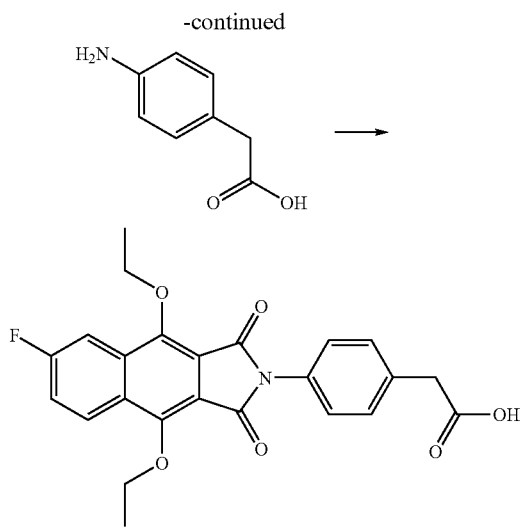

4-Aminophenylacetic acid (418 mg, 2.77 mmol) was added to 1,4-bis(ethyloxy)-6-fluoro-2,3-naphthalenedicarboxylic acid (810 mg, 2.5 mmol) and powdered molecular sieves (4 Å, 200 mg) in NMP (4.5 ml) and heated in a microwave at 180° C. for 10 minutes. The reaction mixture was cooled and diluted with EtOAc, filtered through celite, washed with water, brine, dried over magnesium sulphate and concentrated in vacuo to yield a yellow solid. This was recrystallised from methanol (~50 ml) and the white solid filtered, washed with methanol and dried in vacuo in an oven to give the title compound as a white solid (490 mg, 1.1 mmol). The filtrate was concentrated in vacuo and the yellow oil purified by reverse phase chromatography eluting with acetonitrile: water (1:20-1:0) to give the title compound as a white solid (107 mg, 0.24 mmol).

LC/MS: Rt=3.39, [MH]$^+$ 438.

Description 5

{4-[4,9-Bis(ethyloxy)-6-fluoro-3-hydroxy-1-oxo-1,3-dihydro-2H-benzo[f]isoindol-2-yl]phenyl}acetic acid and {4-[4,9-bis(ethyloxy)-6-fluoro-1-hydroxy-3-oxo-1,3-dihydro-2H-benzo[f]isoindol-2-yl]phenyl}acetic acid

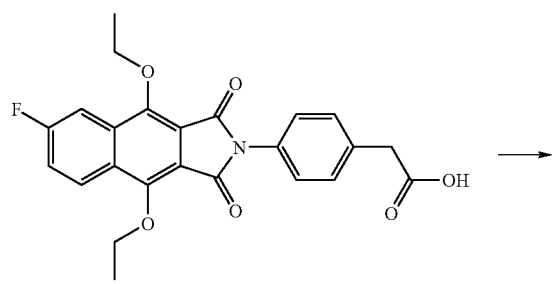

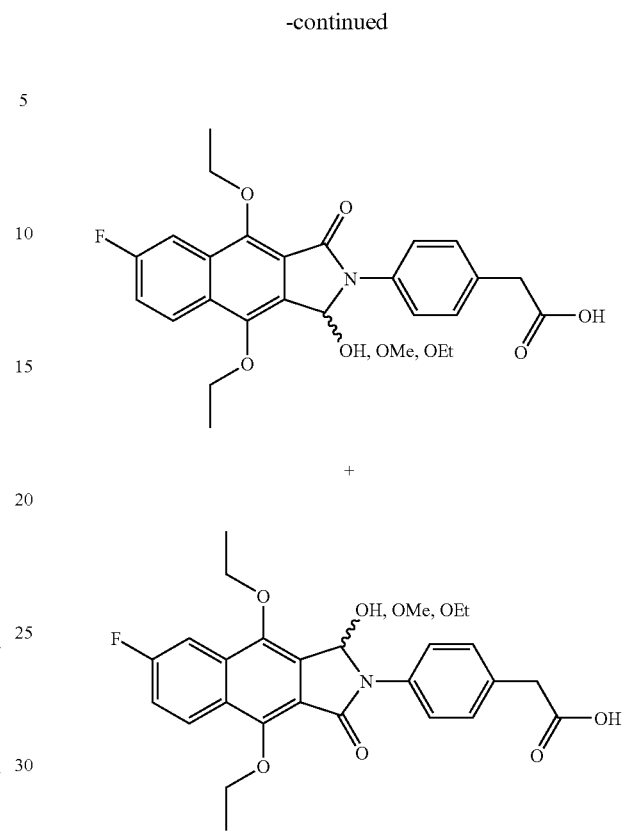

{4-[4,9-Bis(ethyloxy)-6-fluoro-1,3-dioxo-1,3-dihydro-2H-benzo[f]isoindol-2-yl]phenyl}acetic acid (410 mg, 0.94 mmol) was suspended in methanol (8 ml) and THF (12 ml) added until in solution. Sodium borohydride (71 mg, 1.88 mmol) was added and the solution stirred at room temperature. After 17 hours further sodium borohydride (71 mg, 188 mmol) was added, then further sodium borohydride (422 mg, 11.1 mmol) was added portionwise, and ethanol (8 ml) added, over the next 3.5 hours. The reaction was quenched by the addition of 2M HCl (~40 ml) until acidified. Volatiles were removed in vacuo (~50 ml) and the solution then extracted with EtOAc (100 ml). The organics were washed with brine, dried over magnesium sulphate and concentrated in vacuo to give the title compounds as a yellow oil (~500 mg), as a mixture with their methoxy and ethoxy animals.

LC/MS: Rt=2.98 [MH]$^+$ 440, 3.34 [MH]$^+$ 454, 3.47 [MH] 468.

Description 6

{4-[4,9-Bis(ethyloxy)-6-fluoro-1-oxo-1,3-dihydro-2H-benzo[f]isoindol-2-yl]phenyl}acetic acid and
{4-[4,9-bis(ethyloxy)-7-fluoro-1-oxo-1,3-dihydro-2H-benzo[f]isoindol-2-yl]phenyl}acetic acid

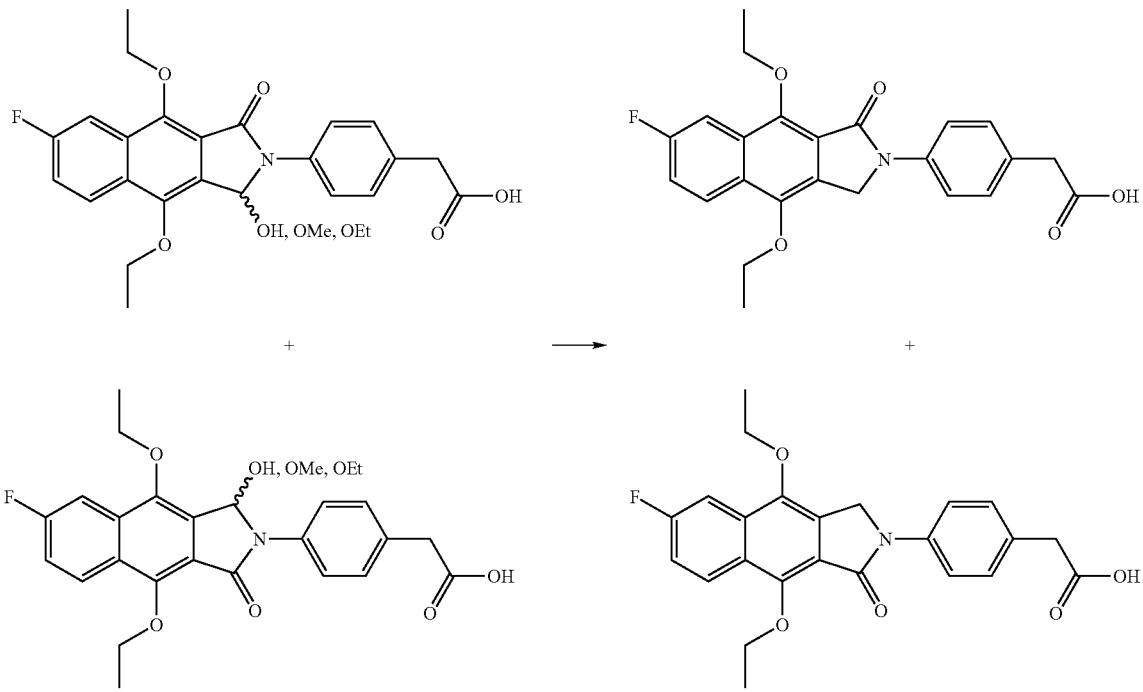

The mixture of {4-[4,9-bis(ethyloxy)-6-fluoro-3-hydroxy-1-oxo-1,3-dihydro-2H-benzo[f]isoindol-2-yl]phenyl}acetic acid and {4-[4,9-bis(ethyloxy)-6-fluoro-1-hydroxy-3-oxo-1,3-dihydro-2H-benzo[f]isoindol-2-yl]phenyl}acetic acid and their methoxy and ethoxy animals (~500 mg, ~0.94 mmol) was treated with TFA (2 ml) and $CH_2Cl_2$ added. Triethylsilane (0.225 ml, 1.4 mmol) was added and stirred at room temperature. Volatiles removed in vacuo to yield an off white solid. This was triturated in $Et_2O$, filtered and dried to yield the title compounds as a mixture of isomers, as a white solid (310 mg, 0.73 mmol) in a 3:2 ratio (by $^1$H NMR). The filtrate was filtered again, the solid washed with $Et_2O$ and dried to yield the title compounds as a white solid (41 mg, 0.1 mmol) in a 3:2 ratio (by $^1$H NMR).

LC/MS: Rt=3.36 [MH]$^+$ 424.

The isomers were separated using supercritical fluid chromatography to yield the 2 separate isomers:

Example 2

{4-[4,9-Bis(ethyloxy)-6-fluoro-1-oxo-1,3-dihydro-2H-benzo[f]isoindol-2-yl]phenyl}acetic acid

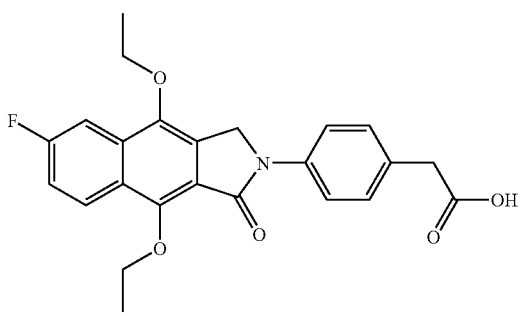

LC/MS: Rt=3.30 [MH]$^+$ 424.

Example 3

{4-[4,9-Bis(ethyloxy)-7-fluoro-1-oxo-1,3-dihydro-2H-benzo[f]isoindol-2-yl]phenyl}acetic acid

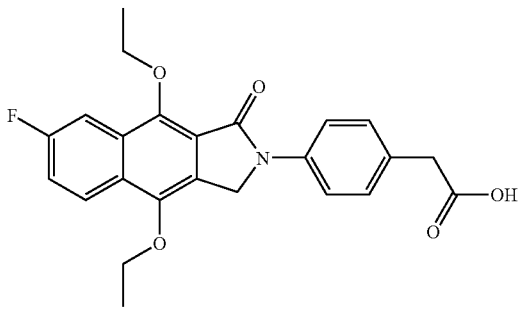

LC/MS: Rt=3.29 [MH]+ 424.

Biological Data

Studies were performed using HEK-293(T) cells expressing the recombinant human prostanoid $EP_4$ receptor (HEK-$EP_4$ cells). Cells were grown as a monolayer culture in DMEM-F12/F12 containing glutamax II (Gibco) and supplemented with 10% foetal bovine serum and 0.4 mg.ml-1 G418. HEK-$EP_4$ cells were pre-treated 24 hr and 30 mins prior to the experiment with 10 μM indomethacin and harvested using Versene containing 10 μM indomethacin. The cells were resuspended in assay buffer (DMEM:F12, 10 μM indomethacin and 200 μM IBMX) at 1×10⁶ cells per ml and incubated for 20 min at 37° C. Thereafter, 50 μl of cells were added to 50 ul agonist (compound of Formula (I)) and incubated at 37° C. for 4 minutes before stopping reactions with 100 μl of 1% triton X-100. cAMP levels in the cell lysates were determined using a competition binding assay. In this assay the ability of cell lysates to inhibit 3H-cAMP (Amersham) binding to the binding subunit of protein kinase A was measured and cAMP levels were calculated from a standard curve. The data for each compound were expressed as a % of the response to a 10 nM maximal concentration of the standard agonist PGE2. For each compound the maximal response and concentration of compound causing 50% of its maximal response were calculated. Intrinsic activity is expressed relative to the maximal response to PGE2. Unless stated, reagents were purchased commercially from Sigma.

The examples of the present invention were tested in the above-mentioned assay and exhibited $pEC_{50}$ values of 7.0 or higher and intrinsic activities of 50% or higher.

What is claimed is:

1. A compound of formula (I) or pharmaceutically acceptable salt thereof,

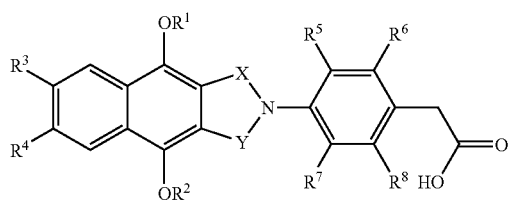

(I)

wherein, $R^1$ and $R^2$ independently represent $C_{1-4}$ alkyl or $C_{1-4}$ haloalkyl;

$R^3$ and $R^4$ independently represent H or F, provided that at least one of $R^3$ and $R^4$ represents F;

$R^5$ and $R^7$ independently represent H, methyl, methoxy, F, Cl or Br;

$R^6$ and $R^8$ independently represent H or F, provided that when one of $R^6$ or $R^8$ represents F then the adjacent atom $R^5$ or $R^7$ represents H; and X and Y independently represent C=O or $CH_2$, provided that at least one of X and Y represents C=O.

2. A compound according to claim 1, wherein $R^1$ and $R^2$ are the same and represent $C_{1-4}$ alkyl.

3. A compound according to claim 2, wherein $R^1$ and $R^2$ are the same and represent ethyl.

4. A compound according to claim 1, wherein $R^3$ represents H and $R^4$ represents F.

5. A compound according to claim 1, wherein $R^3$ represents F and $R^4$ represents H.

6. A compound according to claim 1, wherein $R^5$, $R^6$, $R^7$ and $R^8$ represent H.

7. A compound according to claim 1, wherein both X and Y represent C=O.

8. A compound according to claim 1, having the formula (IA) or a pharmaceutically acceptable salt

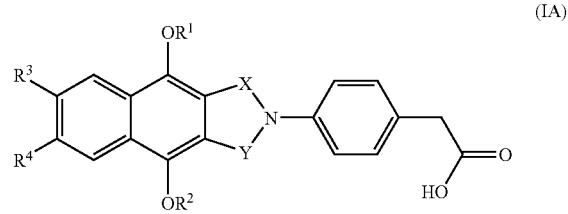

(IA)

thereof, wherein, $R^1$ and $R^2$ independently represent $C_{1-4}$ alkyl;

$R^3$ and $R^4$ independently represent H or F, provided that they are not the same and that at least one of $R^3$ and $R^4$ represents F; and X and Y independently represent C=O or $CH_2$, provided that at least one of X and Y represents C=O.

9. A compound according to claim 1 selected from the group consisting of:

{4-[4,9-bis(ethyloxy)-6-fluoro-1-oxo-1,3-dihydro-2H-benzo[f]isoindol-2-yl]phenyl}acetic acid;

{4-[4,9-bis(ethyloxy)-6-fluoro-1,3-dioxo-1,3-dihydro-2H-benzo[f]isoindol-2-yl]phenyl}acetic acid; and {4-[4,9-bis(ethyloxy)-7-fluoro-1-oxo-1,3-dihydro-2H-benzo[f]isoindol-2-yl]phenyl}acetic acid; or a pharmaceutically acceptable derivative salt thereof.

10. A process for preparing a compound according to claim 1 or a pharmaceutically acceptable salt thereof wherein X and Y represent C=O and $R^1$ to $R^8$ are as defined in claim 1, which process comprises reacting a compound of formula (II),

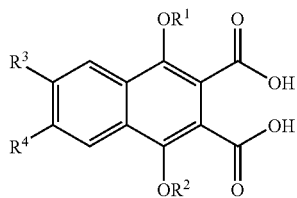

wherein, $R^1$, $R^2$, $R^3$ and $R^4$ are as defined in claim 1, with 4-aminophenylacetic acid or a derivative thereof, and optionally thereafter forming a pharmaceutically acceptable salt of the compound so formed and optionally converting one compound of formula (I) to another.

11. A process for preparing a compound of claim 1 or a pharmaceutically acceptable salt thereof, wherein one of X and Y represents C=O and the other represents $CH_2$, and $R^1$ to $R^8$ are as defined in claim 1, which process comprises reacting a compound of formula (III),

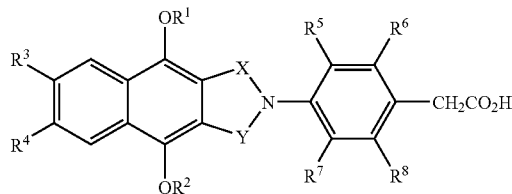

wherein, one of X and Y represents C=O and the other represents CH—OH and $R^1$ to $R^8$ are as defined in claim 1; with a suitable acid followed by a suitable reducing agent, and optionally thereafter forming a pharmaceutically acceptable salt of the compound so formed and optionally converting one compound of formula (I) to another.

12. A process for preparing a compound according to claim 1 or a pharmaceutically acceptable salt thereof, wherein X and Y represent C=O and $R^1$ to $R^8$ are as defined in claim 1, which process comprises reacting a compound of formula (IV),

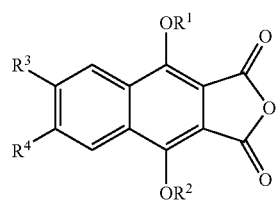

wherein, $R^1$ to $R^4$ are as defined in relation to claim 1, with 4-aminophenylacetic acid or a derivative thereof, and optionally thereafter forming a pharmaceutically acceptable salt of the compound so formed and/or converting one compound of formula (I) to another.

13. A method of treating a human or animal subject suffering from a condition selected from the group consisting of pain, bone disease, bone generation, bone remodeling, and bone fracture which comprises administering to said subject an effective amount of a compound according to claim 1.

14. A pharmaceutical composition comprising a compound according to claim 1 and one or more acceptable carriers or diluents therefor.

15. A pharmaceutical composition according to claim 14, comprising one or more additional therapeutic agents selected from the group consisting of paracetamol and ibuprofen.

16. The method of claim 13 wherein said pain is chronic articular pain and said bone disease is osteoporosis, rheumatoid arthritis, periodontitis, or osteoarthritis.

* * * * *